United States Patent [19]

Patel et al.

[11] Patent Number: 4,911,919

[45] Date of Patent: Mar. 27, 1990

[54] HAIR STRAIGHTENING CONDITIONER

[75] Inventors: Amrit Patel, Dayton; Harry Greenland, Martinsville, both of N.J.

[73] Assignee: Colgate-Palmolive Company, Piscataway, N.J.

[21] Appl. No.: 233,930

[22] Filed: Aug. 12, 1988

Related U.S. Application Data

[63] Continuation of Ser. No. 875,147, Jun. 17, 1986, abandoned.

[51] Int. Cl.$^4$ .............................. A61K 7/06; A61K 7/09
[52] U.S. Cl. ........................................ 424/70; 424/47; 424/59; 424/71; 424/125; 514/938
[58] Field of Search ............................ 424/125, 70, 71

[56] References Cited

U.S. PATENT DOCUMENTS

| | | | |
|---|---|---|---|
| 4,144,326 | 3/1979 | Luedicke, Jr. et al. | 424/70 |
| 4,149,551 | 4/1979 | Benjamin et al. | 424/70 |
| 4,160,823 | 7/1979 | Watanabe et al. | 424/70 |
| 4,183,917 | 1/1980 | Iwao et al. | 424/70 |
| 4,206,196 | 6/1980 | Davis | 424/70 |
| 4,269,824 | 5/1981 | Villamarin et al. | 424/70 |
| 4,275,055 | 6/1981 | Nachtigal et al. | 424/70 |
| 4,421,740 | 12/1983 | Burton | 424/70 |
| 4,436,722 | 3/1984 | Matsunaga et al. | 424/70 |
| 4,530,830 | 7/1985 | McKaba et al. | 424/70 |

FOREIGN PATENT DOCUMENTS

| | | | |
|---|---|---|---|
| 166232 | 1/1986 | European Pat. Off. | 424/70 |
| 56-22716 | 3/1981 | Japan | 424/70 |
| 56-169616 | 12/1981 | Japan | 424/70 |
| 57-50909 | 3/1982 | Japan | 424/70 |
| 58-4709 | 1/1983 | Japan | 424/70 |
| 58-124713 | 7/1983 | Japan | 424/70 |
| 2074184 | 10/1981 | United Kingdom | 424/70 |

OTHER PUBLICATIONS

Wilkinson, et al., *Harry's Cosmeticology*, p. 647 (1983), 7a ed.
Sagarin, *Cosmetics Science and Technology*, pp. 345–352 (1972).

*Primary Examiner*—Dale R. Ore
*Attorney, Agent, or Firm*—Richard J. Ancel; Robert C. Sullivan; Murray M. Grill

[57] ABSTRACT

A stable hair straightening conditioner which softens and conditions hair when used as a rinse conditioner and which straightens hair when left in the hair using a one-step treatment process, consisting essentially of effective amounts of a nonionic water-soluble cellulose polymer, polyvinyl pyrrolidone, a di-$C_{10}$-$C_{22}$ alkyl di-$C_1$-$C_3$ alkyl quaternary ammonium compound, a $C_8$-$C_{18}$alkylamido $C_2$-$C_3$ alkyl di $C_1$-$C_2$ alkyl amine, propylene glycol, mineral oil, a $C_8$-$C_{18}$ alkanol and cyclomethicone in an aqueous vehicle. Also within the scope of the invention is the process of straightening the hair which comprises the steps of applying the straightener-conditioner composition to wet or dry hair in an amount sufficient to wet the hair, combing the hair to distribute the composition and continuing said combing in the presence or absence of added heat until the hair is substantially dry.

7 Claims, No Drawings

HAIR STRAIGHTENING CONDITIONER

This is a continuation of co-pending application Ser. No. 875,147 filed on Jun. 17, 1986.

FIELD OF INVENTION

The present invention relates to a novel hair conditioner which provides body and wet and dry combability properties when used as a rinse conditioner and which softens, straightens the hair when left therein without rinsing, using a novel one-step treatment process. This latter one-step treatment process comprises the application of the product to dry or damp hair in an amount sufficient to make it wet, combing the hair to evenly disperse said product throughout the hair and continuing combing the hair until dry. Optionally, a hair drier may be used during the combing step. The essential components of this composition are a di-$C_{10}$–$C_{22}$ alkyl quaternary ammonium compound such as dicetyl dimethylammonium chloride, $C_{14}$–$C_{18}$ saturated alcohol, $C_7$–$C_{17}$ alkyl amido $C_2$–$C_3$ alkyl di $C_1$–$C_2$ alkyl amine, mineral oil, cyclomethicone, propylene glycol, hydroxyethyl cellulose or hydroxypropylmethyl cellulose and polyvinyl pyrrolidone in an aqueous medium having a pH of 4 to 6. When using distearyldimethylammonium chloride as the quaternary ammonium compound, urea is a preferred additional component. On the other hand, when dihydrogenated tallow dimethylammonium chloride is the quaternary ammonium compound, d-glucose is a preferred additional ingredient in order to optimize the degree of lengthening the hair.

BACKGROUND AND PRIOR ART

Hair conditioners are mainly intended to improve the combability of disturbed or weakened hair resulting from shampooing or chemical treatments, such as bleaching or permanent waving and straightening or weathering or natural causes. Hair straighteners usually are applied to hair having a tight curl, e.g., afro or negroid hair which is subject to spontaneous knotting by entanglement with neighboring hair shafts, resulting in high stress when combed.

Historically, temporary straightening of hair has been achieved by passing a heated metal comb through the hair with the aid of a pressing oil or cream. The oil acts as a heat conductor and lubricant so that the comb can slide through the hair without pulling and sticking. The pressing cream normally contains mineral oil, lanolin, wax, fatty alcohol, polyethylene glycol (PEG) stearate, etc. Additionally, semi-permanent straightening can be achieved by chemical hair straighteners presently on the market which are based on sodium hydroxide, lithium hydroxide, sulfite or thioglycolate, etc. The chemical hair straighteners break the disulfide bond of the hair to form a straight configuration either by relinking the disulfide bond or by forming a new covalent bond according to *The Chemistry of Cosmetics and Manufacture* by Maison G. deNavarre. Thus, these chemical hair straighteners react with hair, change the structure of the hair and finally straighten the hair for a period which lasts through many shampoos.

The disadvantages of the prior art hair relaxing or straightening compositions and procedures using harsh chemicals are irritation to scalp/skin due to the high pH (10–12) of the caustics or similar compounds; hair cuticle uplifting; extensive cuticle damage caused by the caustic; hair becomes dry and dull; sebum flow from scalp is reduced because of cuticle damage; and the structure in the hair is changed because many of the chemical bonds of the hair such as the disulfide bonds are broken and only some are reformed into new covalent bonds.

U.S. Pat. No. 4,530,830 has addressed the problem of the irritancy of the harsh chemicals used in the hair straightening compositions by using 2% to 20%, preferably 2.5% to 8%, by weight of a quaternary ammonium hydroxide as the straightening agent in place of the sodium hydroxide in an emulsion form in order to reduce the irritating tendency exhibited by some of the quaternary ammonium hydroxides at some use concentrations. The aqueous emulsion also contains 2–20% nonionic-emulsifier such as polyethylene glycol ether of cetyl or lauryl or lanolin alcohol, 2–30% of an emollient such as cetyl alcohol, stearyl alcohol, paraffin, mineral oil and lanolin alcohol, and optionally a humectant such as propylene glycol, glycerin, sorbitol or hexylene glycol. This composition is massaged into the hair, left on the hair for ten minutes, again massaged into the hair and washed completely out of the hair. The quaternary ammonium hydroxide straightening agent affects the chemical structure of the hair similarly to the sodium hydroxide and is unlike the present unique hair conditioner and straightener which provides good conditioning, but does not change any chemical structure in the hair.

In the field of hair conditioning, the prior art is replete with hair conditioning compositions containing one or more of the components of the present novel and unique hair conditioner-straightener compositions. For example, U.S. Pat. No. 4,275,055 discloses compositions containing a stearamidopropyldimethyl amine conditioning agent and U.S. Pat. Nos. 4,149,551 and No. 4,206,196 disclose conditioning articles having a di-higher alkyl dimethyl ammonium chloride or a fatty alcohol conditioning agent on a flexible substrate such as paper and the like. In U.S. Pat. Nos. 4,421,740 and 4,269,824, a composition is disclosed which employs the combination of di(hydrogenated tallow) dimethyl ammonium chloride, cetyl or stearyl alcohol and hydroxyethyl cellulose. U.S. Pat. No. 4,436,722 discloses the combination of distearyl dimethyl ammonium chloride, cetyl alcohol and propylene glycol in a hair conditioning compositions. U.S. Pat. Nos. 4,144,326 and 4,160,823 disclose similar compositions which include the combination of distearyl dimethyl ammonium chloride and propylene glycol; and U.S. Pat. No. 4,183,917 discloses a hair conditioner composition which comprises the combination of distearyl dimethyl ammonium chloride, mineral oil, cetyl alcohol and propylene glycol. However, U.S. Pat. Nos. 4,160,823; 4,436,722; 4,269,824 and 4,421,740 equate the mono-higher alkyl quaternary ammonium chloride with a di-higher alkyl quaternary ammonium chloride as the effective conditioning agent in their compositions and, therefore, teach away from the instant unique composition which is specific to the di-higher alkyl quaternary ammonium salts because it has been found that the substitution of a mono-higher alkyl quaternary compounds for the di-higher alkyl compounds in the present composition adversely affects the conditioning properties thereof.

However, it is noted that none of the above cited patents discloses a hair conditioner-straightener composition comprising the mixture of a di-higher alkyl quaternary ammonium compound, a $C_8$–$C_{18}$ amido $C_2$–$C_3$ alkyl di-$C_1$–$C_2$ alkyl amine, a $C_{14}$–$C_{18}$ alcohol, mineral oil, cyclomethicone, a hydroxy alkyl cellulose polymer, polyvinyl pyrrolidone and propylene glycol as the essential ingredients emulsified in an aqueous medium.

SUMMARY OF THE INVENTION

It has been found that a hair straightening conditioning composition comprising the mixture of di-$C_{10}$–$C_{22}$ alkyl di-$C_1$–$C_3$ alkyl ammonium compound, $C_7$–$C_{17}$ alkyl amido $C_2$–$C_3$ alkyl di-$C_1$–$C_2$ alkyl amine, a saturated $C_{14}$–$C_{18}$ alcohol, mineral oil, cyclomethicone, a nonionic water soluble cellulose polymer, polyvinyl pyrrolidone and propylene glycol dispersed in an aqueous medium having a pH of 4 to 6 provides a stable composition having straightening properties as well as very good conditioning properties, including good body, luster, combability and strengthening of the hair. This composition achieves straightening without chemically altering the hair.

Accordingly a primary object of present invention is to provide a hair conditioning composition which also straightens the hair and provides good body to the hair, without damaging the hair.

Another object of present invention is to provide a non-irritating conditioner which is capable of being applied to dry as well as wet hair.

Still another object of present invention is to provide a non-irritating conditioner which is capable of being applied daily after shampooing.

A further object of present invention is to provide a hair straightener -conditioner composition that serves as a rinse conditioner which imparts body and good wet and dry combing properties to the hair.

Another object of present invention is to provide a conditioning composition in the form of a mousse which remains in the hair to soften, strengthen, straighten and style the hair.

Still another object of present invention is to provide a simple, quick and economical one-step treatment process of conditioning, styling and straightening the hair comprising applying the product to the hair and combing the hair until it is dry in order to disperse the product and straighten the combed hair.

Additional objects, advantages and novel features of the invention will be set forth in part in the description which follows and, in part, will become apparent to those skilled in the art.

To achieve the foregoing and other objects and in accordance with the present invention as embodied and broadly described herein, the novel hair straightener conditioner composition of this invention consists essentially of about 0.5% to 2.5% by weight of a di-$C_{10}$–$C_{22}$ alkyl di-$C_1$–$C_3$ alkyl quaternary ammonium compound, about 0.5% to 2.0% by weight of $C_7$–$C_{17}$ alkylamido, $C_2$–$C_3$ alkyl di-$C_1$–$C_2$ alkyl amine, about 1% to 10% by weight of a saturated $C_{14}$–$C_{18}$ alkanol, about 0.2% to 1.5% by weight mineral oil, about 0.1% to 2% by weight of cyclomethicone, about 0.25 to 2.5% by weight of a nonionic water soluble cellulose polymer, about 0.02% to 1% by weight of polyvinylpyrrolidone and about 0.2% to 2% by weight propylene glycol, in about 76.5% to 97.2% by weight of an aqueous carrier. The final product is in the form of an amulsion and has a pH of about 4–6 and preferably 4.5 to 5.5.

The present invention also relates to a novel one-step process of conditioning, styling and straightening the hair which comprises the steps of applying the aforesaid hair straightener-conditioner composition to damp or dry hair in an amount sufficient to wet the hair, combing the hair to distribute said composition on the hair and continuing said combing in the presence or absence of heat until the hair is substantially dry. Preferably, the combing is continued in the presence of heat, e.g., while blow drying the hair, in order to reduce the time required to achieve substantially dry hair.

In a preferred aspect, the present invention relates to a stable hair straightener-conditioner composition having a pH of about 4.5 to 5.5 consisting essentially of, by weight, about 0.7% to 2% of a quaternary ammonium compound selected from the group consisting of di $C_{12}$–$C_{18}$ alkyl dimethyl quaternary ammonium chloride, distearyl dimethyl quaternary ammonium chloride and di-hydrogenated tallow dimethyl quaternary ammonium chloride, about 0.75 to 1.5% of $C_{13}$–$C_{17}$ alkylamidopropyl dimethyl amine, about 1.5% to 4% of cetyl or stearyl alcohol, about 0.3% to 1.0% mineral oil, about 0.2% to 1% of cyclomethicone, about 0.5% to 1.5% of hydroxyethyl cellulose, about 0.05% to 0.5% of polyvinylpyrrolidone and about 0.4% to 1.5% of propylene glycol emulsified in 87% to 95.6% of water, provided that when distearyl dimethyl ammonium chloride is said quaternary salt, 1% to 2% by weight of urea is present and when di-hydrogenated tallow dimethyl ammonium chloride is said quaternary salt, from 1% to 3% by weight of d-glucose is present.

The described hair conditioner compositions are stable, opaque liquids at room temperature. Further, these compositions are stable at 5° C., and at 38° C. to 48° C. It is believed that these compositions are oil-in-water emulsions, with the two cationic compounds being the emulsifying agents.

As indicated, these compositions contain safe chemicals which are not irritating to the skin, are non-toxic are effective to improve the manageability of the hair. It is believed that the good conditioning properties are imparted to the hair when the composition is applied to the hair with or without subsequent rinsing due to the use of the essential mixture of conditioning agents, namely, di-$C_{10}$–$C_{22}$ alkyl $C_1$–$C_3$ alkyl ammonium salt, $C_7$–$C_{17}$ alkylamido $C_2$–$C_3$ alkyl amine salt, $C_{14}$–$C_{18}$ saturated alkanol and mineral oil. Such mixture is readily removed in the course of normal shampooing and does not build-up on the hair. Additionally, it provides a balanced conditioning effect and better hair luster than is normally provided by the mixture of cationic conditioning compounds and said $C_{14}$–$C_{18}$ saturated alkanol. Furthermore, the mixture of cationic compounds serves as the emulsifier to yield the desired physical stability.

On the other hand, the hair straightening effects are believed to be due to the co-action of all of the essential ingredients in the composition. More specifically, the hair relaxing effects of the mixture of conditioning agents on the hair is believed to be rendered semi-permanent due to the formation of a plasticized film of the mixed nonionic cellulose polymer and the polyvinlpyrrolidone. It is thought that the mixture of propylene glycol, mineral oil and volatile dimethyl polysiloxane serve to plasticize the film so that it remains resilient and is non-tacky, but adherent to the surface of the conditioned hair strands. Thus, it is the coaction and interaction of all of the claimed essential ingredients that results in the formation of a stable, liquid hair straightener-conditioner product which is effective to achieve an increase of 13% to 25% in the length of tightly curled hair.

DETAILED DESCRIPTION OF THE INVENTION

The long chain dialkyl ($C_{10}$–$C_{22}$) quaternary salts which are one of the essential compounds in mixture of conditioning agents have been used in the prior art as hair conditioning agents. They are substantially water insoluble cationic surfactants, but stable aqueous dispersions thereof can be obtained in 4–8% concentrations. They are soluble in isopropanol, methanol and ethanol. Generally, these suitable cationic quaternary ammonium salts have the following formula:

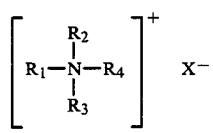

wherein $R_1$ and $R_2$ are aliphatic groups of 10 to 22 carbon atoms, $R_3$ and $R_4$ are each alkyl groups of 1 to 3 carbon atoms and X is an anion selected from the group consisting of chloride, bromide and methyl sulfate. The aliphatic groups may contain ether groups as well as amido groups in addition to carbon and hydrogen, but preferably $R_1$ and $R_2$ are saturated hydrocarbon groups. Representative examples of satisfactory quaternary ammonium salts include distearyl dimethyl ammonium chloride, di-hydrogenated tallow dimethyl ammonium chloride, dilauryl dimethyl ammonium chloride, dihexadecyl dimethyl ammonium chloride, ditetradecyl diethyl ammonium bromide, dicetyl ($C_{12}$–$C_{18}$) dimethyl ammonium chloride, di-docosyl dipropyl ammonium bromide, and dieicosyl diethyl ammonium methyl sulfate. Preferred dialkyl quaternary ammonium salts are dicetyl dimethyl ammonium chloride identified as Adogen 432 CG wherein the dicetyl group is a $C_{12}$–$C_{18}$ alkyl containing, by weight, 16% of $C_{12}$, 23% of $C_{13}$, 13% of $C_{14}$, 1% of $C_{15}$, 24% of $C_{16}$, 14% of $C_{18}$ and 1% of $C_{20}$, distearyl dimethyl ammonium chloride in combination with 1–2% of urea and di(hydrogenated tallow) dimethyl ammonium chloride in combination with 1–3% by weight of d-glucose and the most preferred quaternary salt is the Adogen 432 C.G.

As indicated above, the preferred di $C_{10}$–$C_{22}$ alkyl quaternary ammonium salts include the mixture of distearyl dimethyl ammonium chloride with 1% to 2% by weight of urea and the mixture of di(hydrogenated tallow) dimethyl ammonium chloride with 1% to 3% by weight of d-glucose. In the prescribed amounts, each of urea and d-glucose enhances the straightening effects of the particular di $C_{10}$–$C_{22}$ alkyl quaternary salt. This effect is specific to the particular di $C_{10}$–$C_{22}$ alkyl ammonium salt and similar effects are not observed when these materials are used in combination with the other preferred compound, namely, the dicetyl quaternary compound purchased under the name Adogen 432 CG. Thus, the reason for the enhanced effects is not understood and is truly surprising.

The $C_{10}$–$C_{22}$ dialkyl di-$C_1$–$C_3$ alkyl ammonium salts used in present hair conditioning composition may be obtained from a number of suppliers either in the form of a liquid or paste in an aqueous-isopropanol solvent at 25° C. or in the form of a solid. For example (di-tallow) ammonium chloride may be purchased from Armak as a 74%–77% active paste in aqueous isopropanol containing 74–75% A.I. (active ingredient). The preferred dicetyl ($C_{12}$–$C_{18}$) dimethyl ammonium chloride is obtainable from Sherex Chemical Company in the form of a 74% A.I. paste in aqueous-isopropanol under the name Adogen 432 CG Distearyl dimethyl ammonium chloride also is obtainable from the Sherex Chemical Co. in the form of a dry, free-flowing, white powder under the name Arosurf TA 100. The di $C_{10}$–$C_{22}$ alkyl di $C_1$–$C_3$ alkyl ammonium salt is used in an amount of about 0.5% to 2.5%, preferably 0.7% to 2%, by weight of the composition.

The second component of the conditioning mixture employed in the hair straightener-conditioner compositions also is a cationic material, namely, $C_7$–$C_{17}$ alkyl amido $C_2$–$C_3$ alkyl di $C_1$–$C_2$ alkyl amine salt, which has been employed as a conditioning agent in prior art compositions. Examples of suitable cationic amines include stearamidopropyl dimethylamine, lauramidopropyl dimethylamine, cocoamidopropyl dimethylamine, palmitamidopropyl dimethylamine, myristamidoethyl dimethylamine and stearamidopropyl diethyl amine. (The foregoing list names the compounds based upon the alkanoic acid from which the amide is derived, e.g., stearamido is derived from the reaction of stearic acid and an organic amine, but the more proper nomenclature would be heptadecylamido because the amido group is a —$C(O)N^{50}$ radical.) Preferred amines are the $C_{13}$–$C_{17}$ alkyl amidopropyl dimethyl amines, with heptadecyl amidopropyl dimethyl amine being the most preferred. The proportion of said higher alkylamido lower alkyl di-lower alkyl amine in the final composition is about 0.5% to 2%, preferably 0.75% to 1.5%, by weight.

In the straightener-conditioner compositions, the $C_7$–$C_{17}$ alkylamido $C_2$–$C_3$ alkyl di $C_1$–$C_2$ alkyl amine compound is present in the form of an acid salt. Such salt is formed when the amine base is neutralized with a water-soluble acid to form the acidic cationic salt. Acids which are suitable for neutralizing the cationic amine include citric acid, acetic acid, lactic acid, tartaric acid, gluconic acid, hydrochloric acid and phosphoric acid with citricacid being preferred. The amount of acid used should be sufficient to obtain a composition having a pH of 4–6 and preferably about 4.5 to 5.5.

In the straightener-conditioner product, the dialkyl quaternary salt and the alkyl amidoamine salt are the primary hair conditioning agents and are the emulsifiers. Additionally, the $C_8$–$C_{18}$ alkyl amido $C_2$–$C_3$ alkyl di-$C_1$–$C_2$ alkylamine salt is effective to modify the film of cationic material deposited on the hair so that the heavy coated feeling characteristic of the di-higher alkyl quaternary salts is minimized. Thus, the proportions of the two cationic compounds are controlled in the range of 10:1 to 1:5, preferably 2:1 to 1:2 with respect to one another, said ratio being of dialkyl quaternary salt to alkyl amido amine salt.

The third compound in the mixture of conditioning agents is a $C_{14}$–$C_{18}$ saturated alkanol. Since the preferred alkanols are obtained from fats and oils, these alkanols are often referred to as fatty alcohols. However, alkanols made by synthetic processes also are satisfactory. Examples of suitable alkanols are 1-tetradecanol, 1-hexadecanol, 1-heptadecanol, 1-octadecanol and mixtures of $C_{14}$–$C_{18}$ alkanols obtained by hydrogenating the fatty acids derived from tallow. Preferred higher alkanols are stearyl alcohol and cetyl alcohol. The proportion of $C_{14}$–$C_{18}$ alkanol present in straightener-conditioner composition is about 1% to 10%, preferably 1.5% to 4%, by weight. Furthermore, the $C_{14}$–$C_{18}$ alkanol usually is the predominant compound in the mixture of conditioning agents because it is present in the largest percentage. Typically, the weight ratio of $C_{14}$–$C_{18}$ alkanol to the total cationic surfactants ranges from about 2:1 to 0.75:1.

The final essential compound in the mixture of hair conditioning agents is mineral oil-another compound employed in prior art hair conditioning products. Mineral oil is a homogeneous mixture of saturated aliphatic and alicyclic hydrocarbons derived from petroleum. Mineral oil is chemically and biologically inert and is hydrophobic in nature. Mineral oil is available in various viscosities. The proportion of mineral oil present in the straightener-conditioner composition is about 0.2% to 1.5%, preferably 0.3 to 1.0%, by weight. Usually, the mineral oil represents less than 20% by weight of the mixture of the four conditioning agents and preferably less than 10% by weight of said mixture. Such controlled small amounts of mineral oil tend to counteract the dulling effects of the cationic surfactants by enhancing the shine of the hair and also function as a plasticizer for the film forming polymers present in the final composition.

Another essential ingredient in the hair conditioning compositions is a water-soluble, nonionic, cellulose polymer which functions both as a thickening agent and as a film forming agent. Suitable cellulosic polymers are selected from the group consisting of hydroxyethyl cellulose and hydroxypropyl methyl cellulose, with hydroxyethyl cellulose being preferred. Hydroxyethyl cellulose is the product of reaction between an alkali cellulose and ethylene oxide, and such products are available in a number of viscosity grades. Viscosity is primarily dependent upon the viscosity of the cellulose used in the reaction. The degree of substitution of hydroxyethyl groups per glycose unit is 1.4–1.5, the hydroxyethyl molar substitution is 1.5–3.0, and these hydroxyethyl celluloses have an average molecular weight range from about 80,000 to about 900,000. A particularly preferred hydroxyethyl cellulose is available under the tradename Natrosol 250 HR from Hercules, Inc.. Water-soluble hydroxypropyl methyl cellulose has a methyoxyl content between about 25% and about 32% by weight and a hydroxypropyl content between about 2% and 10%, preferably 2% to 7%, by weight. Again, the chain length of the cellulose used in the reaction can be controlled to provide a molecular weight which yields a viscosity for a 2% solution in water in the range of 10 cps and 5000 cps, preferably 50 cps to 4000 cps.

These cellulose polymers provide stability to the composition upon aging by viscosity control. The composition retains its viscosity without thinning out or thickening. In addition to controlling the viscosity of the aqueous hair straightener-conditioner composition, the cellulose polymer contributes to the hair straightening properties by forming a film on the hair coated with the described mixture of conditioning agents. It appears that this nonionic cellulose cooperates with the other film forming polymer to form a film on the hair having the mixture of conditioners thereon by hydrogen bonding with the cationic surfactants. The resultant film adheres to the hair and maintains its stiffness without delaminating between shampooings. The proportion of nonionic cellulose polymer is about 0.25% to 2.5%, preferably 0.5% to 1.5%, by weight of the hair straightener-conditioner composition.

The other essential film forming polymer in the hair straightener-conditioner composition is a water soluble, nonionic polyvinylpyrrolidone. Polyvinylpyrrolidone (PVP) is available in an average molecular weight range from about 10,000 to 360,000 and the type known commercially as PVP K-30 having an average molecular weight of about 40,000 is preferred. Polyvinylpyrrolidone is available in the form of a powder (contains about 95% of polymer and 5% water) and in the form of an aqueous solution. It is believed that the polyvinylpyrrolidone cooperates with the cellulose polymer to form a clear, substantially stiff film on the hair which retains the shape of the hair and also is smooth and pliable so that it does not interfere with combing. The amount of polyvinylpyrroliddine is about 0.02% to 1%, preferably 0.05% to 0.5%, by weight of the final composition. Also, the polyvinylpyrrolidone usually is a minor amount of the mixture of polymers, i.e., about 4% to 15% by weight of the polymer mixture, so that a smooth, substantially non-tacky film is obtained. Amounts of polyvinylpyrrolidone in excess of 1% by weight yield a film which is too rigid and too tacky.

The film formed by the coaction of the PVP with the nonionic cellulose polymer is plasticized by the combination of propylene glycol, and mineral oil. Propylene glycol is a clear, viscous, colorless liquid which is hygroscopic and is completely miscible with water. Propylene glycol can penetrate both the polymer film and the hair shaft and remain there after rinsing. The effect of this material is believed to result in a softening and swelling of the polymer film and the hair as well as providing a humectant effect to the film, i.e., it enables the polyvinylpyrrolidone-cellulose polymer film to retain its moisture and flexibility between shampooings. The amount of propylene glycol used in the final composition is about 0.2% to 2% preferably 0.4% to 1.5%, by weight.

Another essential component is cyclomethicone which is a volatile cyclic silicone represented by the formula:

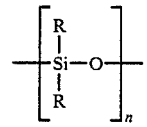

wherein R is a $C_1$–$C_3$ alkyl group or a phenyl group, preferably a methyl group; n is a number from 3 to 10, preferably 3 to 7, and the unsatisfied valencies on the oxygen and silicon atoms at the end of the chain are joined together to form a cyclic structure. Suitable cyclic silicones are available as low viscosity fluids from a number of manufacturers, including the General Electric Company. The most preferred cyclomethicones are decamethyl cyclopentasiloxane (General Electric's Silicone Fluid SF 1202) and octamethyl cyclotetrasiloxane (General Electric's Silicone Fluid SF 1173).

The cyclic silicones are non-polar, insoluble in water and completely miscible in lower alcohols, aliphatic aromatic solvents and halogenated hydrocarbon solvents. This ingredient facilitates the distribution of the mixture of conditioning agents on the hair and the quick spreading of the polymers on the hair. The proportion of volatile cyclic silicone in the hair straightener-conditioner composition is about 0.1% to 2%, preferably 0.2% to 1.0%, by weight.

The final essential ingredient in the hair straightener-conditioner composition is an aqueous medium which is primarily water. Since some of the di $C_{10}$–$C_{22}$ alkyl di $C_1$–$C_3$ alkyl quaternary salts may be supplied in admixture with a $C_2$–$C_3$ alcohol, e.g., isopropanol, the aqueous medium usually contains a small amount of said $C_2$–$C_3$ alcohol. Furthermore, if desired, additional amounts of $C_2$–$C_3$ alkanol may be added to the composition, particularly where the composition is sold in the form of a "mousse". The proportion of the aqueous medium is in the range of 76.5% to 97.2%, preferably 87% to 95.6%, most preferably 90% to 95.0% by weight of the hair rinse composition. Usually, the $C_2$–$C_3$ alkanol will be a very minor proportion of the aqueous medium, ranging from 0% to 1% by weight of the hair rinse composition, with the higher amounts of such alkanol being present in the "mousse" compositions.

The pH of the hair conditioner of the present invention is acidic and ranges from about 4 to 6, preferably about 4.5 to 5.5.

The coaction of all the nine aforedescribed essential components unexpectedly provides a uniquely superior hair straightening conditioner product which is non-irritating. The omission of a single component adversely affects the unique properties of the total composition. Accordingly, the criticality of all nine ingredients and the specificity of each ingredient is necessary in the formulation of the present novel hair product. Furthermore, the present hair composition has a dual function because it can be used as a rinse conditioner to provide body and good wet and dry combing properties to the treated hair or it can also be used as a hair straightener composition to straighten and lengthen the hair.

When employed as a hair straightener, a simple, safe process of straightening the hair is achieved which consists essentially of the steps of applying the composition to damp or dry hair in an amount sufficient to wet the hair, distributing said composition throughout the hair by combing and continuing the combing in the presence or absence of heat until the hair is substantially dry. Preferably, the step of continuing the combing is carried out while simultaneously drying the hair with warm or hot air from a hair drying apparatus in order to shorten the time required to achieve substantially dry hair. For example, the period of combing can be reduced from ten minutes to about two minutes when a blow drier is employed. Obviously, the amount of aqueous hair straightener-conditioner composition varies with the amount of hair of the user. Usually from 2 to 20, preferably from 5 to 10, milliliters (ml) of product will be sufficient to wet the hair of a woman having hair of medium length.

The foregoing hair straightening process is quicker, less costly and far superior to the prior art commercial, two-step, chemical treatment process of applying a hair relaxing composition for a period of time, followed by the application of a neutralizer to the hair and removal of excess neutralizer by rinsing. Such treatment often takes at least one hour of time and costs up to $50.00; whereas, hair straightening is accomplished by the inventive compositions at a low cost and in a short period of time. More specifically, the preferred compositions contain a low concentration of essential ingredients, e.g., 4% to 13% by weight, and provide the same conditioning effects as commercial products containing 65% by weight of essential ingredients.

As described heretofore, optionally desirable components in the present hair conditioning and straightening composition include about 1–2% by weight of urea or 1% to 3% by weight of d-glucose when either distearyl dimethyl ammonium chloride or di(hydrogenated tallow) dimethyl ammonium chloride is employed in the composition.

The hair straightener-conditioner in accordance with the invention may be in the form of a pourable lotion or a smooth cream. Further, the final product may have any suitable viscosity so long as it is appropriate for the final form selected, e.g., a pourable lotion, a thick or viscous lotion or a cream.

The hair straightener-conditioner compositions of this invention also may contain conventional additional components such as coloring agents, perfumes, preservatives such as formaldehyde (formalin) and brighteners such as Uvinul. The total weight of these optional additives usually does not exceed 5% by weight of the composition and preferably does not exceed 2% by weight of the composition, with the proportion of the individual ingredients usually being less than 1% by weight.

The present hair straightener-conditioner compositions can be manufactured readily by simple mixing methods. For example, a preferred method of preparing the present compositions comprises the steps of dispersing the hydroxyethyl cellulose in water and mixing while heating to 80°–85° C. until a uniform, clear, lump-free solution is obtained; adding the propylene glycol, the di $C_{10}$–$C_{22}$ alkyl quaternary ammonium compound and an acid to adjust pH (citric acid) in sequence with mixing while maintaining the temperature at 80°–85° C. to form a uniform aqueous solution; forming a separate mixture of the remaining water-insoluble ingredients, name $C_{14}$–$C_{18}$ alkanol, $C_7$–$C_{17}$ alkylamido $C_2$–$C_3$ alkyl di-$C_1$–$C_2$ alkyl amine, mineral oil and cyclomethicone, and heating said mixture to a temperature of about 70° C. to 85° C.; adding the mixture of water-insoluble ingredients to the aqueous mixture with slow agitation while maintaining the temperature in the range of 80° C. to 85° C.; cooling the resultant emulsion at 35° C. to 45° C. with slow agitation; admixing an aqueous solution of polyvinylpyrrolidone in water with said emulsion while continuing the agitation; adding any optional ingredients to the foregoing mixture; and cooling the resultant composition to 25° C. to 30° C. in the presence of slow agitation to form a stable, opaque emulsion having a pH in the range of 4 to 6. Any required adjustment of pH usually is made during the cooling step by adding an appropriate concentration of acid or alkali metal hydroxide.

The following examples merely illustrate the invention, but it is understood that the invention is not limited thereto. All amounts of various ingredients in the examples and elsewhere in the specification are by weight unless otherwise specified.

EXAMPLES 1–3

Hair Straightener Conditioner

| Examples 1–3 Hair Straightener Conditioner | 1 | 2 | 3 |
|---|---|---|---|
| Stearyl Alcohol | 2.50 | 2.50 | 2.50 |
| Stearamidopropyl Dimethylamine | 1.00 | 1.00 | 1.00 |
| Mineral Oil | 0.50 | 0.50 | 0.50 |

-continued

Examples 1-3
Hair Straightener Conditioner

|  | 1 | 2 | 3 |
|---|---|---|---|
| Cyclomethicone[a] | 0.25 | 0.25 | 0.25 |
| Propylene Glycol | 0.50 | 0.50 | 0.50 |
| Deionized Water | 92.17 | 92.90 | 92.65 |
| Hydroxyethylcellulose[b] | 1.00 | 1.00 | 1.00 |
| Citric Acid | 0.20 | 0.20 | 0.20 |
| Polyvinylpyrrolidone[c] | 0.10 | 0.10 | 0.10 |
| Perfume | 0.20 | 0.20 | 0.20 |
| Formalin | 0.10 | 0.10 | 0.10 |
| Dicetyl Dimonium Chloride[d] | 1.48 | — | — |
| Distearyl Dimonium Chloride[e] | — | 0.75 | — |
| Di(hydrogenated tallow)[f] Dimonium Chloride | — | — | 1.00 |

[a] Purchased from General Electric as Silicone Fluid SF 1202
[b] Purchased from Hercules as Natrosol 250H
[c] Purchased from GAF Corporation as PVP K-30
[d] Purchased from Sherex Chemical sa Adogen 432 CG which contains 74% by weight of ($C_{12}$—$C_{18}$) dialkyl ammonium chloride having the following alkyl distribution by weight: $C_{12}$ - 16%, $C_{13}$ - 23%, $C_{14}$ - 13%, $C_{15}$ - 9%, $C_{16}$ - 24%, $C_{18}$ - 14%, and $C_{20}$ - 1%
[e] Purchased from Sherex Chemical under the name Arosurf TA-100
[f] Purchased from Armak as a 75% dispersion in aqueous isopropanol under the name Arquad 2HT (The alkyl distribution by weight is 4% $C_{14}$, 31% $C_{16}$ and 64% $C_{18}$.

In preparing the hair straightener conditioner of Example 1, the hydroxyethylcellulose is dispersed in deionized water and mixed until a uniform clear solution is obtained, and heated to 80°-82° C. with mixing. The propylene glycol, the long chain alkyl quaternary chloride and citric acid are added to, and mixed with the aqueous hydroxyethyl cellulose solution at 80°-82° C. until a uniform aqueous solution is obtained. The stearyl alcohol, stearamidopropyl dimethylamine, mineral oil and cyclomethicone are slowly mixed and heated to 80°-82° C. in a small mixer until a uniform clear solution is obtained, which is slowly added to, and mixed with the aqueous solution at 80°-82° C. After addition is completed, the emulsion mixture is mixed for another 20 minutes and slowly cooled to 38°-40° C. Polyvinylpyrrolidone dissolved in 1% deionized water is added to the emulsion at 38°-40° C. with mixing and mixing is continued while the composition is cooled at 25°-30° C. The perfume and formalin are added to the emulsion at 25°-30° C. with mixing. The final products are white smooth pourable lotions which are stable under all conditions of aging.

The compositions of Examples 1-3 are readily spreadable and distribute well throughout the hair when applied directly to the hair using the fingers. Also, wet and dry combing are very good and the treated hair has softness and body. Further, the hair is easily styled, straightened and lengthened. Maximum conditioning properties are obtained when the conditioner is applied to the hair without rinsing. Such use of this conditioner has application as a hair styling mousse.

The procedure for straightening the hair comprises the following steps.

A sufficient amount of the lotion, e.g., 2 to 20 ml, exemplified is applied to the hair and using the fingers is worked into the hair for about 60 seconds to assure thorough saturation. Then, the lotion wetted hair is combed to detangle the hair and evenly distribute the lotion throughout the hair. Thereafter, the hair is blow dried while constantly combing until substantially dry. The effectiveness of the compositions is straightening the hair is set forth in Table I below wherein the length of hair tresses treated with the compositions of Examples 1-3 are compared with a similar tress which is shampooed only as well as with other tresses which have been shampooed and treated with commercially available hair conditioner compositions. In each evaluation, the individual hair tress —3.25 grams of virgin Negroid hair having a length of 8-13 centimeters (cm)—is shampooed with 1.0 ml of an aqueous shampoo containing 10% by weight of sodium lauryl triethenoxy ether sulfate for about one minute and thereafter rinsed with 40° C. water for about one minute prior to being squeezed dry and being treated with the 1.0 milliliter (ml) of test conditioner-straightener product. The straightening ability or property of the inventive compositions is indicated by the increase in length of the hair tress and all measurements are expressed in centimeters. Table I follows:

TABLE I
Straightening Test

|  | Control | Ex. 1 | Ex. 2 | Ex. 3 | Commercial Conditioner A[2] | Commercial Conditioner B[3] |
|---|---|---|---|---|---|---|
| Initial Length After SLES[1] Wash | 7.8 | 7.7 | 8.0 | 8.4 | 12.8 | 12.8 |
| Length After 1.0 ml Conditioner Treatment | 7.8 | 9.6 | 9.4 | 9.5 | 12.9 | 13.0 |
| Length Increase | 0.0 | 1.9 | 1.4 | 1.1 | 0.1 | 0.2 |
| Percentage Increase | 0 | 25 | 17 | 13 | 1 | 2 |

[1] Sodium lauryl triethenoxy ether sulfate containing shampoo
[2] Commercial conditioner A contains 2% by weight of dicetyl dimonium chloride as the principal conditioning agent.
[3] Commercial conditioner B contains 1% by weight of $C_{20}$—$C_{22}$ alkyl trimethyl ammonium chloride as the principal conditioning agent.

Table I clearly shows the unexpectedly superior straightening properties and tress lengthening properties of the present novel conditioners. An increase of 1.1 to 1.9 cm in hair length is obtained with present conditioners as compared to only 0.1 to 0.2 cm for typical commercially available conditioners. As indicated, the formulation of Example 2 with dicetyl dimonium chloride exhibits a 25% increase in the tress length and clearly is the most preferred straightener product.

A second application of conditioner on top of the first conditioner application does not additionally increase the length of the hair. Likewise, when the alternate shampoo-conditioner sequence is repeated three times, no additional increase in the length of the hair is noted. Accordingly, it is the first application of this conditioner that effects the increase in the length of the tress.

When the above formulations are used as a rinse-off conditioner instead of as a conditioner-straightener, they are effective conditioners as evidenced by the results of the wet combing tress test listed in Tables II and III. In the wet combing tests, tresses of negroid hair are shampooed with shampoo containing 10% SLES for one minute, rinsed with 40° C. water for one minute, squeezed dry, treated with the test conditioner for one minute and rinsed with 40° C. water for one minute. Thereafter, the tresses are combed while wet and rated for combability on a scale from one—the rating for hair which is shampooed only—to five—the rating for hair which is shampooed and treated with a good, effective rinse conditioner. This means that a rating of five indicates a good, effective conditioner, and a rating of one denotes a poor conditioner or shampoo wash. Thus, on the basis of these results the instant conditioner-lengthener composition is considered to be a heavy conditioner when used as a rinse conditioner. (The results in Tables II and III are the average of six readings and the combability tests were done by six combing experts).

TABLE II

| | Wet Combability Results | | | |
|---|---|---|---|---|
| | Shampoo | Ex. 1 | Commercial Conditioner[A] | Commercial Conditioner[B] | Effective Conditioner Control |
| Avg. | 1.00 | 5.55 | 4.55 | 4.25 | 5.00 |

As indicated above, these results are obtained after one cycle, and one cycle is a shampoo treatment followed by a conditioner treatment. These results are quite significant because it has been noted that Negroid hair is very hard to comb without the help of a conditioner.

Examples 4 and 5 set forth other preferred conditioner-straightener compositions wherein the straightening effects of distearyl ammonium chloride are enhanced by the presence of 2% by weight of urea and the straightening effects of dihydrogenated tallow dimonium chloride are enhanced by the presence of 2% by weight of d-glucose.

| | % By Weight | |
|---|---|---|
| Ingredient | Example 4 | Example 5 |
| Stearyl Alcohol | 2.50 | 2.50 |
| Stearamidopropyl/dimethylamine | 1.00 | 1.00 |
| Mineral Oil | 0.50 | 0.50 |
| Cyclomethicone | 0.25 | 0.25 |
| Propylene Glycol | 0.50 | 0.50 |
| Deionized Water | 90.90 | 90.65 |
| Hydroxyethylcellulose | 1.00 | 1.00 |
| Citric Acid | 0.20 | 0.20 |
| Polyvinylpyrrolidone | 0.10 | 0.10 |
| Perfume | 0.20 | 0.20 |
| Formalin | 0.10 | 0.10 |
| Distearyl Dimonium Chloride (e) | 0.75 | — |
| Di(Hydrogenated tallow) Dimonium Chloride (f) | — | 1.00 |
| Urea | 2.00 | — |
| d-Glucose | — | 2.00 |

When the compositions of Examples 4 and 5 are employed in the procedure reported in Table I, the length of the hair tress is increased by 1.7 cm—21%—and by 1.7 cm—22%—respectively and such increases are greater than the increase noted for similar compositions containing the same di($C_{12}$-$C_{18}$) alkyl dimonium salt, but neither urea nor d-glucose. Furthermore, it is noted that these preferred compositions of Examples 4 and 5 yield increases in hair length comparable to those obtained using the most preferred dicetyl dimonium quaternary salt.

Another satisfactory conditioner composition which is a stable lotion at temperatures of 4° C., 24° C., and 38° C. is obtained when 1.5% by weight of dilauryl dimonium chloride is substituted for the dicetyl dimonium chloride in the composition of Example 1. Dilauryl dimonium chloride is purchased from Humko under the name Kemamine Q-6902 C having an alkyl distribution by weight of 5% $C_{10}$, 90% $C_{12}$ and 5% $C_{14}$. This salt contains 75% by weight of said dialkyl dimonium chloride.

Other satisfactory conditioner-straightener compositions which are effective rinse conditioners are set forth in Examples 7-9.

| | Examples 7-9 | | |
|---|---|---|---|
| Ingredients | 7 | 8 | 9 |
| Cetyl Alcohol | 2.00 | 2.00 | 2.00 |
| Stearamidopropyl Dimethylamine | 1.00 | 1.00 | 1.00 |
| Mineral Oil | 0.25 | 0.25 | 0.25 |
| Cyclomethicone | 0.25 | 0.25 | 0.25 |
| Propylene Glycol | 0.25 | 0.25 | 0.25 |
| Hydroxyethylcellulose | 1.00 | 1.00 | 1.00 |
| Citric Acid | 0.20 | 0.20 | 0.20 |
| Polyvinylpyrrolidone | 0.10 | 0.10 | 0.10 |
| Perfume | 0.20 | 0.20 | 0.10 |
| Formalin | 0.10 | 0.10 | 0.10 |
| Dicetyl Dimonium Chloride (a) | 1.50 | — | — |
| Distearyl Dimonium Chloride (Arosurf TA-100) | — | 0.75 | — |
| Di-(hydrogenated tallow) Dimonium Chloride(Arquad 2HT-75) | — | — | 1.00 |
| Deionized Water | 93.15 | 93.90 | 93.75 |

The compositions of Examples 7-9 are low cost formulations and contain a lower level of solids (active ingredients), but are effective hair rinse conditioners as shown by the wet combing tests in Table III.

TABLE III

| | Wet Combing Test | | | |
|---|---|---|---|---|
| | | Example | | Commercial |
| Shampoo | 7 | 8 | 9 | Conditioner[B] |
| Avgs. 1.0 | 7.16 | 6.16 | 6.16 | 5.00 |

The preceding results are the average of six readings. The results are obtained after one cycle which comprises a shampoo treatment, rinsing, a conditioner treatment and rinsing. Some of the tabulated values exceed the maximum rating of 5 on the 1-5 scale because the evaluators felt that the experimental formulas were superior to the product which was considered to give a 5 in wet combability.

The results of a study conducted on 20 subject to determine and evaluate the performance efficacy and the consumer perception of instant hair straightener/-conditioner product show the test product was rated on the Moderately Easy-Very Easy level for wet hair parameters of snag removal, combing ease and blow drying ease and on the Moderately Good/Extremely Good level for the dry hair parameters of combing ease, soft feel and dryness/oiliness.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A hair straightener-conditioner composition consisting essentially of about 0.5% to 2.5% by weight of a di-$C_{10}$-$C_{22}$ alkyl di-$C_1$-$C_3$ alkyl quaternary ammonium compound; about 0.5% to 2.0% by weight of $C_7$-$C_{17}$ alkylamido $C_2$-$C_3$ alkyl di-$C_1$-$C_2$ alkyl amine; about 1% to 10% by weight of a saturated $C_{14}$-$C_{18}$ alkanol; about 0.2% to 1.5% by weight mineral oil; about 0.1% to 2% by weight of a cyclic silicone of the formula

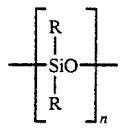

wherein R is a $C_1$–$C_3$ alkyl group or phenyl group and n is a number for 3 to 10; about 0.25% to 2.5% by weight of a nonionic water soluble cellulose polymer; about 0.02% to 1% by weight of polyvinylpyrrolidone; and about 0.2% to 2% by weight of propylene glycol in about 76.5% to 97.2% by weight of an aqueous medium, said composition being in the form of an emulsion and having a pH of about 4-6, said di-$C_{10}$–$C_{22}$ alkyl quaternary ammonium compound being selected from the group consisting of di-$C_{12}$–$C_{18}$ alkyl dimethyl ammonium chloride, distearyl dimethyl ammonium chloride and di-hydrogenated tallow dimethyl ammonium chloride, said di-$C_{10}$–$C_{22}$ alkyl quaternary ammonium compound containing distearyl dimethyl ammonium chloride in combination with 1% to 2% by weight of urea.

2. A composition according to claim 1, said di-$C_{10}$–$C_{22}$ alkyl quaternary ammonium compound containing dihydrogenated tallow dimethyl ammonium chloride in combination with 1-3% by weight of d-glucose.

3. A composition according to claim 1 wherein said di-$C_{10}$–$C_{22}$ alkyl quaternary compound is present in an amount of 0.7% to 2.0% by weight; said alkyl amine is a $C_{13}$–$C_{17}$ alkyl amidopropyl dimethyl amine and is present in an amount of 0.75% to 1.5% by weight; said alkanol is stearyl alcohol or cetyl alcohol and is present in an amount of 1.5% to 4% by weight; said mineral oil is present in an amount of 0.3% to 1% by weight; said cellulose is a hydroxyethyl cellulose having an average molecular weight in the range of 80,000 to 900,000 and is present in an amount of 0.5% to 1.5% by weight; said cyclic silicone is a dimethyl silicone wherein n is 3 to 7 and is present in an amount of 1.2% to 1% by weight; said polyvinylpyrrolidone is present in an amount of 0.05% to 0.5% by weight; said propylene glycol is present in an amount of 0.4% to 1.5% by weight, said aqueous medium is water and is present in an amount of 87% to 95.6% by weight; said composition having a pH of 4.5 to 5.5 and being effective to straighten hair such that a negroid hair tress is increased in length by at least 20%.

4. A composition according to claim 3, wherein said di-$C_{10}$–$C_{22}$ alkyl quaternary ammonium compound is distearyl dimethyl ammonium chloride.

5. A composition according to claim 4 additionally containing 1% to 2% by weight urea.

6. A composition according to claim 4, wherein said di-$C_{10}$–$C_{22}$ alkyl quaternary ammonium compound is di-hydrogenated tallow dimethyl ammonium chloride.

7. A composition according to claim 6 additionally containing 1% to 3% by weight of d-glucose.

* * * * *